United States Patent [19]

Ward

[11] 4,367,356

[45] Jan. 4, 1983

[54] PROCESS FOR THE PRODUCTION OF GASOLINE FROM C4 HYDROCARBONS

[75] Inventor: Dennis J. Ward, South Barrington, Ill.

[73] Assignee: UOP, Inc., Des Plaines, Ill.

[21] Appl. No.: 272,594

[22] Filed: Jun. 11, 1981

Related U.S. Application Data

[63] Continuation-in-part of Ser. No. 122,154, Feb. 19, 1980, abandoned.

[51] Int. Cl.³ .............................................. C07C 2/58
[52] U.S. Cl. .................................. 585/315; 585/329; 585/331
[58] Field of Search ................ 585/329, 331, 314, 315

[56] References Cited

U.S. PATENT DOCUMENTS

| | | | |
|---|---|---|---|
| 2,419,692 | 4/1947 | Shoemaker et al. | 585/240 |
| 2,804,490 | 8/1957 | Belden | 585/311 |
| 3,437,706 | 4/1969 | Gantt et al. | 585/450 |
| 3,437,707 | 4/1969 | Sulzbach | 585/450 |
| 3,437,708 | 4/1969 | Gantt | 585/450 |
| 3,510,534 | 5/1970 | Sulzbach | 585/450 |
| 3,686,354 | 8/1972 | Hervert | 585/331 |
| 3,729,526 | 4/1973 | Anderson | 585/706 |
| 3,763,261 | 10/1973 | Sobel | 585/332 |
| 3,800,003 | 3/1974 | Sobel | 585/332 |
| 3,810,955 | 5/1974 | Sobel | 585/300 |
| 3,916,019 | 10/1975 | Closson et al. | 585/511 |
| 3,959,400 | 5/1976 | Lucki | 585/515 |
| 4,098,839 | 7/1978 | Wilms et al. | 585/526 |
| 4,113,790 | 9/1978 | Cesca et al. | 585/532 |
| 4,139,573 | 2/1979 | Carson | 585/701 |
| 4,161,497 | 7/1979 | Makovec et al. | 585/714 |

OTHER PUBLICATIONS

F. Asinger, Mono-Olefins Chemistry and Technology, Pergamon Press, New York, 1968, pp. 444-457 and 464-482.

*Primary Examiner*—Curtis R. Davis
*Attorney, Agent, or Firm*—James R. Hoatson, Jr.; John F. Spears, Jr.; William H. Page, II

[57] ABSTRACT

A process for producing gasoline from a charge stream comprising a mixture of butanes and butylenes is disclosed. The quality of a product alkylate is improved by increasing the butene-2 content of an alkylation zone feed stream. A first portion of the charge stream is passed into a dimerization zone in which isobutylene is reacted with normal butylenes, with butene-1 being reacted to a greater extent than butene-2. A $C_8$ hydrocarbon-containing product stream and a $C_4$ stream having a higher butene-2 concentration than the charge stream are recovered from the dimerization zone. This high butene-2 content $C_4$ stream is admixed with a second portion of the charge stream and passed into an alkylation zone wherein butylenes are reacted with isobutane to yield a second product stream containing $C_8$ hydrocarbons.

10 Claims, 1 Drawing Figure

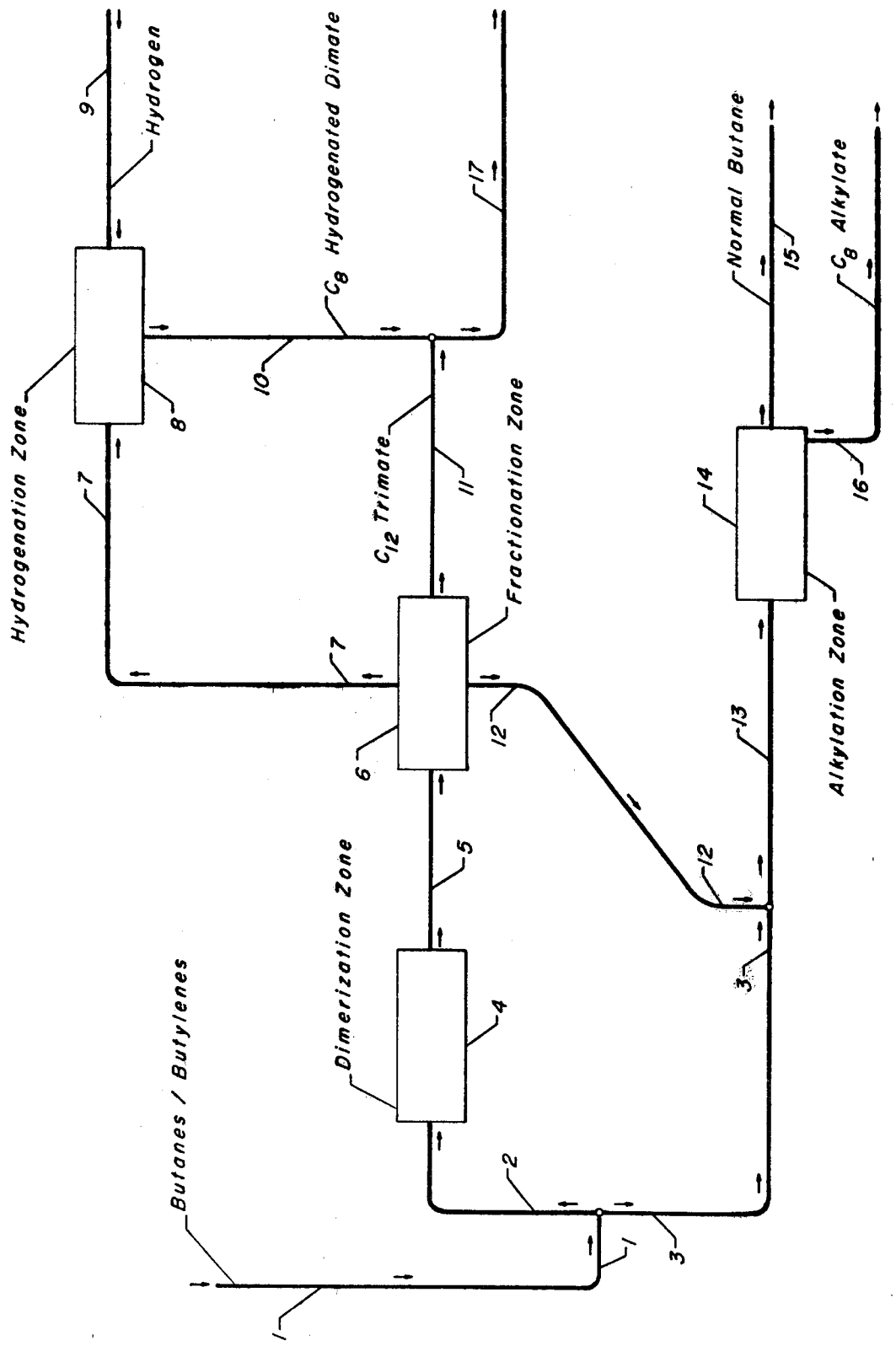

PROCESS FOR THE PRODUCTION OF GASOLINE FROM C4 HYDROCARBONS

CROSS REFERENCE TO RELATED APPLICATION

This application is a continuation-in-part of my prior copending application Ser. No. 122,154 filed Feb. 19, 1980, and now abandoned. The disclosure and teaching of my prior application is incorporated herein.

FIELD OF THE INVENTION

The invention is a novel hydrocarbon conversion process which comprises the dimerization (catalytic condensation) and alkylation of $C_4$ hydrocarbons. The invention is directly related to a process for producing high octane gasoline blending stocks from a mixture of $C_4$ olefins and saturates and in which normal butenes and isobutylene are reacted in the presence of a solid phosphoric acid catalyst in a first reaction zone and mixed butylenes are reacted with isobutane in the presence of a mineral acid catalyst in a second reaction zone. Processes involving these operations may be found in U.S. Patents classified in Classes 208 and 585.

PRIOR ART

The dimerization of light olefins is a well documented chemical reaction. Processes for the oligomerization of light olefins using a heterogeneous catalyst are described in U.S. Pat. Nos. 3,916,019; 3,959,400; 4,098,839 and 4,113,790. Process flow diagrams for oligomerization processes which utilize a solid phosphoric acid (SPA) catalyst are presented in U.S. Pat. Nos. 3,437,706; 3,437,707; 3,437,708 and 3,510,534.

It is known to those skilled in the art that the octane number of a $C_8$ dimate may be increased by passing the dimate through a selective hydrogenation zone.

The use of liquid-phase hydrofluoric acid (HF) as an alkylation catalyst to promote the reaction of isobutane and olefins is described in many references. HF is used to promote this reaction in many large scale commercial alkylation units which produce high octane gasoline blending stocks. The overall process is described in U.S. Pat. Nos. 2,419,692; 3,686,354; 3,729,526; 4,139,573 and 4,161,497 (Cl. 585-714).

A rather complete discussion of the upgrading of light olefins to gasoline blending stocks is provided by *Mono-Olefins Chemistry and Technology* by F. Asinger as translated by B. J. Hazzard, Pergamon Press, New York, 1968, at pages 444–457 and 464–482. This discussion includes a description of the polymerization (dimerization) of butenes to produce isooctane over an SPA catalyst and also a description of the HF-catalyzed alkylation of isobutane with normal butenes. The reference discloses several multistep processes which may include dehydrogenation, polymerization and hydrogenation. The only multistep process in which selective polymerization of specific $C_4$ olefins is perfomed is believed to be that described on page 453 in which isobutene is polymerized under mild conditions thereby leaving straight chain olefins and n-butane for polymerization in a second stage.

On page 474 this reference compares the results of using different $C_4$ olefins in the sulfuric acid-catalyzed alkylation of isobutene. It states the composition of the octane fraction of the alkylates is fairly uniform but that the use of butene-1 gives the most octanes. It is believed this reference does not disclose either the preferential use of butene-2 in alkylation or the fact that a mild dimerization step may be utilized to increase the mole ratio of butene-2 to butene-1 in a mixed $C_4$ stream.

The desirability of using butene-2 as compared to butene-1 as feedstock to an alkylation zone to produce high octane gasoline blending stocks is disclosed in U.S. Pat. No. 2,804,490. U.S. Pat. No. 3,800,003 presents a process in which a feed stream comprising butene isomers is passed into an isomerization zone to increase the quantity of butene-2 available for passage into a downstream alkylation zone.

U.S. Pat. Nos. 3,763,261 and 3,810,955 illustrate processes in which a sorption zone is used to separate butene-1 and butene-2. Alkylation zones are employed in both references to produce gasoline blending stocks. In the latter reference, the butene-1 rich stream is passed into a different alkylation zone than the butene-2 rich stream.

BRIEF SUMMARY OF THE INVENTION

The invention provides an improved process for converting a mixture of olefinic and saturated $C_4$ hydrocarbons into high octane gasoline blending stocks. The process includes the upgrading of an alkylation zone feed stream by the dimerization of butylenes present in a first portion of the feed stream in a manner which produces a residual $C_4$ fraction having a significantly higher butene-2 content than the feed stream. Blending this residual $C_4$ fraction with the remaining undimerized second portion of the feed stream produces a mixture having a higher butene-2 concentration than the feed stream and which therefore produces a higher octane alkylate when charged to an HF alkylation zone than would the original feed stream.

One embodiment of the invention may be characterized as a hydrocarbon conversion process which comprises the steps of dividing a feed stream which comprises normal butane, isobutane, isobutylene and normal butylenes into a first process stream and a second process stream; passing the first process stream into a dimerization zone in which isobutylene is reacted with a normal butylene, and thereby producing a dimerization zone effluent stream comprising isobutane, isobutylene, normal butylenes and $C_8$ hydrocarbons; separating the dimerization zone effluent stream into a first product stream comprising $C_8$ hydrocarbons and a third process stream which comprises isobutane, isobutylene and normal butylenes, with the mole ratio of butene-2 to butene-1 in the third process stream being greater than that of the feed stream; and passing the second process stream and the third process stream into an alkylation zone in which butylenes are reacted with isobutane to produce $C_8$ hydrocarbons, and recovering from the alkylation zone a second product stream which comprises $C_8$ hydrocarbons.

DESCRIPTION OF THE DRAWING

The drawing is a schematic flow diagram of the preferred embodiment of the invention. A feed stream which preferably contains at least 90 mole percent $C_4$ hydrocarbons enters the process through line 1. This feed stream contains isobutane, normal butane, isobutylene, butene-1 and butene-2. The feed stream is divided into two smaller streams with the first stream passing through line 2 to a dimerization zone 4 and with the second stream passing through lines 3 and 13 to an alkylation zone 14. The dimerization zone is operated under conditions which achieve only a limited consumption of normal butenes. This results in the formation of a dimerization zone effluent stream which comprises the unreacted $C_4$ hydrocarbons, butylene dimers and butylene trimers.

The dimerization zone effluent stream is passed through line 5 into a fractionation zone 6. The dimerization zone effluent stream is therein separated into a third process stream carried by line 12 which contains essentially all of the $C_4$ hydrocarbons present in the dimerization zone effluent stream, a stream of butylene dimers carried by line 7, and a stream of butylene trimers carried by line 11. The olefinic $C_8$ dimers carried by line 7 are passed into a hydrogenation zone 8 and therein saturated with hydrogen carried by line 9. The hydrogenation zone effluent stream carried by line 10 comprises the saturated dimers and is admixed with the butylene trimers carried by line 11 to form a first product stream removed from the process through line 17.

Because the dimerization zone is operated at conditions which result in the preferential consumption of butene-1, the $C_4$ hydrocarbon-containing third process stream carried by line 12 has a higher concentration of butene-2 than the original feed stream carried by line 1. The third process stream is admixed with the second portion of the feed stream from line 3 to form an alkylation zone feed stream which contains a higher overall concentration of butene-2 than the original process feed stream. A better quality alkylate is therefore produced when this stream is passed into the alkylation zone 14 through line 13. The alkylation reaction consumes essentially all of the butylenes and isobutane passed into the alkylation zone. A net effluent stream which comprises the residual unreacted normal butane is removed from the alkylation zone in line 15 and a second product stream comprising the $C_8$ alkylate is removed in line 16.

DETAILED DESCRIPTION

There has been a constantly increasing demand for high octane gasoline blending stocks. This is in part the result of the gradual phase-down of lead antiknock compounds in gasoline. It also results from the steadily increasing number of motor vehicles which must be fueled with lead-free gasoline to prevent damage to pollution reduction systems. For these and other reasons, it has become increasingly important to maximize both the quantity and the octane number of gasoline produced from the available feedstocks.

It is an objective of the subject invention to provide a hydrocarbon conversion process for producing high octane motor fuel blending stocks. It is also an objective of the subject invention to provide an improved process for converting a mixture of $C_4$ olefins and $C_4$ paraffins into high octane $C_8$ hydrocarbons in which an alkylation reaction consumes the isobutane in the feed mixture.

In the subject process, high octane gasoline blending components are produced by reacting $C_4$ hydrocarbons in two different reaction zones by two different reactions. These two reaction zones are a dimerization zone in which isobutylene and a normal butene are reacted and an alkylation zone in which isobutane is reacted with normal butenes. The $C_4$ hydrocarbons contained in the feed stream must include isobutane, isobutylene, butene-1 and butene-2. The feed stream will also normally contain some normal butane. In addition some $C_3$ and $C_5$ hydrocarbons may be present in the feed stream, but it is preferred that less than 12 mole percent of all the hydrocarbons in the feed stream have other than four carbon atoms per molecule. A preferred source for the feed stream is the light hydrocarbon off gases of a fluidized catalytic cracking (FCC) unit used to convert high boiling hydrocarbons into more volatile hydrocarbons including those in the gasoline boiling point range. It is preferred that the feed stream contains over 50 mole percent butylenes.

The total feed stream to the process is first divided into two small streams. It is preferred that each of these two streams has a flow rate equal to at least 30 percent of the flow rate of the total feed stream. It is also preferred that the two smaller streams are formed by simply dividing the feed stream into two smaller streams having identical compositions rather than performing any separation operation, such as flashing the feed stream, to create process streams of differing composition.

A first portion of the feed stream is passed into a dimerization zone operated at conditions which purposely limit the conversion which is achieved. One reason for limiting the conversion is that above a certain level of conversion, the octane number of the dimate product begins to decrease. A total conversion therefore produces a lower octane product. The degree of conversion is measured by reference to the consumption of normal butene (butene-1 plus butene-2) since the desired dimerization is the reaction of isobutylene with a normal butene. The reaction conditions should be selected to react no more than two moles of normal butenes per mole of isobutene and preferably less than one mole of normal butene per mole of isobutene. The $C_4$ hydrocarbon stream which is recovered from the dimerization zone preferably contains less than 3.0 mole percent isobutylene.

The linkage of the dimerization zone wih an alkylation zone according to the inventive concept provides a synergistic result. This is because butene-1 is reacted at a much greater rate than butene-2 in the dimerization reaction. Over the preferred catalyst butene-1 is also converted to butene-2 in the dimerization zone, thereby decreasing the overall butene-1 concentration. The $C_4$ hydrocarbons which exit the dimerization zone will therefore have a higher ratio of butene-2 to butene-1 than the feed stream to the dimerization zone or the process. By admixing these residual $C_4$ hydrocarbons, which comprise butene-1, butene-2, isobutylene, isobutane and possibly normal butane, with the second portion of the feed stream there is formed a new stream which also has a higher butene-2 to butene-1 ratio. The passage of this new stream into an alkylation zone as a feed stream will allow the production of a higher octane alkylate than would be produced at the same operating conditions using the original feed stream. In summary, the dimerization zone is utilized as a means to preferentially react butene-1 and to thereby improve the alkylation zone feed stream and the product of the alkylation zone.

The preferred embodiment of the invention may be characterized as a hydrocarbon conversion process which comprises dividing a feed stream which comprises normal butane, isobutane, isobutylene, normal butylenes and which contains less than 12 mole percent of non-$C_4$ hydrocarbons into a first process stream and a second process stream having identical compositions; passing the first process stream into a dimerization zone in which isobutylene is reacted with a normal butylene in the presence of an SPA catalyst, and thereby producing a dimerization zone effluent stream comprising normal butane, isobutane, isobutylene, normal butenes and $C_8$ hydrocarbons; separating the dimerization zone effluent stream into a first product stream comprising $C_8$ hydrocarbons and a third process stream which comprises normal butane, isobutane, isobutylene and normal butylenes and which has a mole ratio of butene-2 to butene-1 greater than 6.0:1.0; admixing the second process stream and the third process stream, passing the resultant admixture into an alkylation zone in which liquid-phase HF is utilized as a catalyst and in which butylenes are reacted with isobutane to produce $C_8$ hydrocarbons, and recovering from the alkylation zone a second product stream which comprises $C_8$ hydrocarbons.

A large number of dimerization catalysts and processes are known and may be employed in the subject process if desired. However, it is preferred that an SPA (solid phosphoric acid) catalyst is used in the dimerization zone. As used herein, the term "SPA catalyst" is intended to indicate a solid catalyst which contains as one of its principal ingredients an acid of phosphorus such as an ortho-, pyro-, or tetra-phosphoric acid. The catalyst is normally formed by mixing the acid of phosphorus with a siliceous, solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives, such as mineral talc, fullers earth and iron compounds including iron oxide may be added to the carrier to increase its strength and hardness. The combinaion of the carrier and the additives preferably comprises about 15-30% of the catalyst, with the remainder being the phosphoric acid. The additive may comprise about 3-20% of the total carrier material. Variations from this such as a lower phosphoric acid content are however possible. Further details as to the composition and production of SPA catalysts may be obtained from U.S. Pat. Nos. 3,050,472; 3,050,473 and 3,132,109 and from other references.

The catalyst is preferably disposed in fixed beds within the dimerization zone. Either a tubular or chamber-type reactor structure may be used. In a tubular reactor, the catalyst is placed in relatively small diameter tubes which are surrounded by a water jacket to remove the heat liberated by the exothermic reaction. Steam generated in this manner can be used to preheat the feed. In a chamber-type reactor, the reactants flow through a series of large diameter catalyst beds. The temperature of the reactants is controlled by recycling relatively inert hydrocarbons which act as a heat sink or by the use of a quench between vertically stacked catalyst beds. The quench material is the same as that used as the recycle stream, and both methods of temperature control may be used simultaneously. The different catalyst beds ae preferably contained within a single, cylindrical, vertically oriented vessels, and the feed stream preferably enters the top of the dimerization reactor. A chamber-type reactor containing about five catalyst beds is preferred.

The dimerization zone is maintained at dimerization-promoting conditions. These conditions may vary widely due to the previously listed variables. A broad range of suitable pressures is from about 15 to about 1200 psig, with a preferred pressure range for an SPA catalyst being from 400 to 1000 psig. The temperature maintained in this zone with the preferred SPA catalyst may vary from about 120° to about 260° C. Steam or water may be fed into the dimerization zone to maintain the desired water content in the preferred catalyst.

In the preferred embodiment, an SPA catalyst is utilized in a chamber-type dimerization zone to form a net effluent containing $C_8$ and $C_{12}$ hydrocarbons. The boiling points of these hydrocarbons, as determined by the appropriate ASTM distillation method, will be within a gasoline boiling point range of about 43° to about 215° C. The feed stream is first commingled with a recycle stream comprising propane and butane which is used as a temperature controlling diluent. It is then heat exchanged with the dimerization zone effluent, further heated and passed into the top of the dimerization reactor. Additional amounts of a propane/butane-rich coolant similar in composition to the recycle stream are added between each of the catalyst beds.

The net effluent of the dimerization zone is separated into at least two and preferably three streams of different composition. It is preferred that this separation is performed in a fractionation zone which comprises two fractionation columns. The first column will act as a stabilizer to remove $C_4$ and lighter hydrocarbons from dimerization zone effluent and to concentrate these light hydrocarbons into a net overhead stream which is the third process stream of the subject process. The bottoms stream of the first column will contain $C_5$-plus hydrocarbons and is preferably passed into a second column in which it is split into a net overhead stream which contains the $C_8$ dimers and a net bottoms stream which contains the $C_{12}$ trimers produced in the dimerization zone. These separations are relatively easy to perform by fractionation using trayed columns operated at atmospheric or superatmospheric pressure.

The separation of the $C_8$-plus product hydrocarbons into a $C_8$-rich fraction and a $C_{12}$-rich fraction is preferred since it facilitates the upgrading of the dimerization zone product. This upgrading is accomplished by passing the olefinic $C_8$ dimers through a hydrogenation zone operated at mild conditions selected to hydrogenate olefins but which do not lead to significant isomerization of the $C_8$ hydrocarbons. The saturation of the dimers increases their octane number. However, it is normally considered impractical to pass the $C_{12}$ trimers into the hydrogenation zone since these trimers are more difficult to hydrogenate and also because high boiling sulfur compounds which tend to poison the hydrogenation catalyst are present in the $C_{12}$ trimer fraction. The hydrogenation may be performed by contacting the dimers with a hydrogenation catalyst, such as nickel on kieselguhr, in admixture with hydrogen at the rate of at least 1,000 standard cubic feet of hydrogen per barrel of hydrocarbons. Suitable hydrogenation conditions include a pressure of between 60 and 200 psig, a temperature of from about 120° to 170° C. and a liquid hourly space velocity of from 1.0 to 5.0 $hr^{-1}$. In this embodiment, the effluent of the hydrogenation zone is admixed with the unhydrogenated $C_{12}$ trimer fraction to produce the liquid product stream withdrawn from the process.

The hydrogenation of the $C_8$ dimers is not an essential step in the subject process. This optional step may therefore be deleted from the process, and the net dimate product stream removed from the process would be a mixture containing $C_8$ and $C_{12}$ olefinic hydrocarbons. This product stream would be withdrawn from the bottom of the stabilizer which removes the $C_4$ hydrocarbons from the dimerization zone effluent stream. Only one fractionation column would therefore be required in the fractionation zone in this embodiment.

The $C_4$ hydrocarbons recovered from the effluent of the dimerization zone are passed into the alkylation zone. It is preferred that these hydrocarbons are admixed with the portion of the process feed stream which does not enter the dimerization zone and that this total admixture is passed into the alkylation zone as a single alkylation zone feed stream. The term "alkylation zone" is intended to indicate a sequence of processing equipment in which the entering reactants are contacted with an alkylation catalyst maintained at alkylation-promoting conditions including one or more reaction zones and the required equipment for the separation and recovery of the resultant alkylate from process streams circulated within the alkylation zone. In many instances, the alkylation zone will include a fractionation zone. This fractionation zone will normally contain two or three fractionation columns used to recover the alkylate and to separate other hydrocarbons and an additional column for catalyst regeneration if HF is used as the catalyst.

The alkylation reaction is promoted by the presence of a mineral acid-catalyst such as hydrofluoric acid, sulfuric acid or phosphoric acid. Although the use of vapor-phase acid is possible, it is greatly preferred that these acids are maintained in a liquid phase which contains a minimum of water to reduce corrosion problems. The maximum amount of water normally allowed in the acid is about 5 wt.%. When fresh acid is charged to a plant, it is normally very dry and contains about 0.5 percent water or less. The catalyst may also comprise a mixture of a mineral acid and a Friedel-Crafts metal halide promoter such as aluminum chloride, aluminum bromide, boron trifluoride and other proton donors.

Alkylation conditions in general include a pressure sufficient to maintain the hydrocarbons and acid in a liquid phase, with a general range being from about 20 to about 500 psig, and a more preferred range being from 100 to about 250 psig. It is preferred that the pressure within the reactant-catalyst contacting vessel is approximately 150 psig and essentially "floats" on the pressure maintained in a downstream fractionation zone. Although the alkylation reaction may be performed at temperatures from below 0° to about 200° F., it is preferred to operate the commercially prevalent isoparaffin-olefin alkylation process in the range of from about 50° to about 140° F., being a representative and particularly preferred operating temperature.

Typical operating conditions in the alkylation zone include a high ratio of the concentration of the paraffinic or other alkylatable material to the concentration of the olefinic material in order to produce a high quality alkylate by encouraging monoalkylation instead of polymerization. A broad range of this ratio is from about 6 to about 20 with a preferred operating range being from 8 to 12. If there is a shortage of isobutane in the alkylation zone, additional isobutane from a supplemental feed stream may be passed directly into the alkylation zone. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.5:1, but it is preferred that the subject process is operated at an acid to hydrocarbon ratio of about 2:1.

There are a great number of olefin-isoparaffin alkylation processes known to those skilled in the art. The great majority of these processes will operate wihin the range of alkylation conditions set out above. They would however have substantial differences in equipment and flow paths used in performing the alkylation. These variations are attempts to obtain optimum quality alkylate by varying the method of contacting the monoolefin with the isoparaffin. Since this reaction occurs very rapidly, and also because hydrofluoric acid will catalyze the polymerization of the monoolefin, the standard alkylation methods consist of either first admixing acid-free streams of olefin and isoparaffin to form a reactant mixture which is then admixed with the hydrofluoric acid, or an acid-free olefin stream is mixed with an acid-containing isoparaffin stream. In either case, a large number of ventures or mixing nozzles are normally utilized to quickly disperse the olefin-containing stream into the acid-containing stream.

The resulting alkylation reaction is very exothermic and it is therefore necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the mixer settler is passed into a fractionation column. This hydrocarbon phase will comprise mainly alkylate and the excess isoparaffin which was fed to the alkylation zone but will also normally contain normal butane present in the alkylation zone feed stream. Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., may be obtained by reference to the previously cited references.

The hydrocarbon phase removed from the settler is preferably passed into a first fractionation column referred to as an isostripper since entering isobutane is concentrated into its net overhead stream. The isostripper produces a net bottoms stream which comprises the $C_8$ alkylate and any $C_5$-plus hydrocarbons and which is removed from the process as a second product stream. When HF is utilized as the alkylation catalyst, some isopentane, and also some propane, is produced in the alkylation reactor. $C_5$ hydrocarbons which were present in the feed stream and which were not affected by passage through the alkylation zone will also be present in this bottoms stream. Substantially all of the normal butane which enters the isostripper will be concentrated into a sidecut stream and removed from the process. It is often acceptable for some butane to also be present in the bottoms stream since this is necessary to meet the volatility standards for gasoline. The overhead stream of the isostripper will contain HF, isobutane and propane. Two additional columns are normally employed to recover the isobutane and HF for recycling to the alkylation zone from the isostripper overhead stream. One conventional method of doing this is to pass the hydrocarbon phase formed by condensing the isostripper overhead into a depropanizer column which concentrates the isobutane into a net bottoms stream. The next overhead of the depropanizer is then fed to an HF stripper which produces a bottoms stream containing the propane. The remaining HF is returned to the alkylation zone.

I claim as my invention:

1. In a hydrocarbon conversion process in which a feed stream comprising isobutane, isobutylene and normal butylenes is passed into an HF alkylation zone and $C_8$ hydrocarbons suitable for use as motor fuel blending components are produced therein, the improvement which comprises increasing the butene-2 content of the feed stream by the series of steps which comprises:
   (a) dividing the feed stream into a first process stream and a second process stream of equal composition;
   (b) passing the first process stream into a dimerization zone in which butylenes are reacted with isobutylene, and thereby producing a dimerization zone effluent stream which comprises isobutane, isobutylene, normal butylenes and $C_8$ hydrocarbons;
   (c) separating the dimerization zone effluent stream into a dimate stream which is rich in $C_8$ hydrocarbons and a third process stream which comprises isobutane, isobutylene and normal butylenes, with the mole ratio of butene-2 to butene-1 in the third process stream being greater than the mole ratio of butene-2 to butene-1 in the feed stream; and,
   (d) passing the second process stream and the third process stream into an alkylation zone in which butylenes are reacted with isobutane as the alkylation zone feed.

2. A hydrocarbon conversion process which comprises the steps of:
   (a) dividing a feed stream which comprises isobutane, isobutylene and normal butylenes into a first process stream and a second process stream;
   (b) passing the first process stream into a dimerization zone in which isobutylene is reacted with a normal butylene, and thereby producing a dimerization zone effluent stream comprising isobutane, isobutylene, normal butylenes and $C_8$ hydrocarbons;
   (c) separating the dimerization zone effluent stream into a first product stream comprising $C_8$ hydrocarbons and a third process stream which comprises isobutane, isobutylene and normal butylenes, with the mole ratio of butene-2 to butene-1 in the third process stream being greater than the mole ratio of butene-2 to butene-1 in the feed stream; and,
   (d) passing the second process stream and the third process stream into an alkylation zone in which butylenes are reacted with isobutane to produce $C_8$ hydrocarbons, and recovering from the alkylation zone a second product stream which comprises $C_8$ hydrocarbons.

3. The process of claim 2 further characterized in that no more than two moles of normal butene are reacted per mole of isobutene within the dimerization zone.

4. The process of claim 3 further characterized in that an SPA catalyst is utilized within the dimerization zone.

5. The process of claim 4 further characterized in that HF is utilized as a catalyst within the alkylation zone.

6. The process of claim 5 further characterized in that the first product stream is passed into a hydrogenation zone wherein $C_8$ olefins are saturated.

7. The process of claim 2 further characterized in that the feed stream comprises 50 mole percent butylenes.

8. The process of claim 7 further characterized in that butene-1 is consumed to a proportionally greater extent than butene-2 in the dimerization zone and in that the mole ratio of butene-2 to butene-1 in the third process stream is greater than 6.0:1.0.

9. The process of claim 8 further characterized in that less than one mole of normal butenes is reacted per mole of isobutene within the dimerization zone.

10. The process of claim 9 further characterized in that less than 12.0 mole percent of the hydrocarbons in the feed stream have other than four carbon atoms per molecule.

* * * * *